(12) United States Patent
Lau

(10) Patent No.: US 6,207,192 B1
(45) Date of Patent: *Mar. 27, 2001

(54) PROLONGATION OF CHEMICAL ACTIVITY OF FLAVORANTS AND THERAPEUTICS WITH CETYL PYRIDINIUM CHLORIDE

(75) Inventor: John R. Lau, Howard, OH (US)

(73) Assignee: SDG, Inc., Wooster, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/315,359

(22) Filed: Sep. 30, 1994

(51) Int. Cl.[7] ............................. A61K 9/10; A61K 9/22; A61K 47/22; A61K 47/18
(52) U.S. Cl. ........................ 424/484; 424/440; 424/441
(58) Field of Search ..................... 424/484, 465, 424/452, 457, 440, 441, 425; 514/964, 970

(56) References Cited

U.S. PATENT DOCUMENTS 5,236,699 * 8/1993 Libin ................................... 424/54

* cited by examiner

*Primary Examiner*—Edward J. Webman
(74) *Attorney, Agent, or Firm*—Fay, Sharpe, Beall, Fagan, Minnich & McKee

(57) ABSTRACT

Cetyl pyridinium chloride and other amphiphilic substances may be mixed with flavorants or therapeutics in accompaniment with such as bulking agents or sweeteners in order to prolong their duration of action at the site of attachment, which is a mucin coated surface for the purpose of providing the consumer with a more efficacious product.

It is the concept of delayed dispensing that is the invention, the product being dispensed is only an illustration of the best mode.

15 Claims, 9 Drawing Sheets

US 6,207,192 B1

PROLONGATION OF CHEMICAL ACTIVITY OF FLAVORANTS AND THERAPEUTICS WITH CETYL PYRIDINIUM CHLORIDE

BACKGROUND OF THE INVENTION

Water soluble organic compounds, such as comestibles and therapeutic agents, are incorporated into syrups or hard candy, as a means of prolonging the activities of active ingredients, such as menthol in breath fresheners, or therapeutic agents.

A simple hard candy throat lozenge is a known means of supplying a therapeutic agent to the oral cavity and esophagus of a warm blooded host. See MUCIN, U.S. Pat. No. 4,921,644.

However, the same simple means is not readily available for prolonging the active time frame for the organic therapeutic compounds, such as p-aminobenzoic acid ethylester. The organic substance cannot be readily incorporated in candy for extended application, because, when the candy is gone, so is the flavorant, such as menthol. Elixir liquid, to be effective, must be limited to fast action, which in turn, effects the treatment time.

OBJECTS OF THE INVENTION

It is an object of the invention to prolong the retention of flavorant taste or soothing action pharmaceuticals, in the oral cavity of a warm-blooded host.

Another object of the invention is to employ a dispenser to extend the time of application of comestibles and therapeutic substances to the oral cavity, esophagus, eye, vagina, bladder, rectal cavity, stomach, and all mucin coated surfaces in the warm-blooded host.

Another object of the invention is to incorporate an organic active substance in a carrier, said carrier having an affinity for mucin and thereby holds the carrier in a desired location to release active substance over a time span.

The reference with respect to affinity to mucin is a statement of a means to anchor the active ingredients in a favorable location, and has no reference to the time extension which is the object of the invention.

SUMMARY

The preferred embodiment of this invention utilizes amphiphilic substances to adhere to mucin surfaces and provides a hydrophobic reservoir which can entrap and sequester organic compounds, comestibles, and therapeutic agents in order to prolong their effect in a warm-blooded host.

DEFINITION

Cetyl pyridinium chloride hereafter will be represented by the acronym: CPC.

Critical micelle concentration will be represented by the acronym: CMC.

DRAWINGS

Figure 4A:
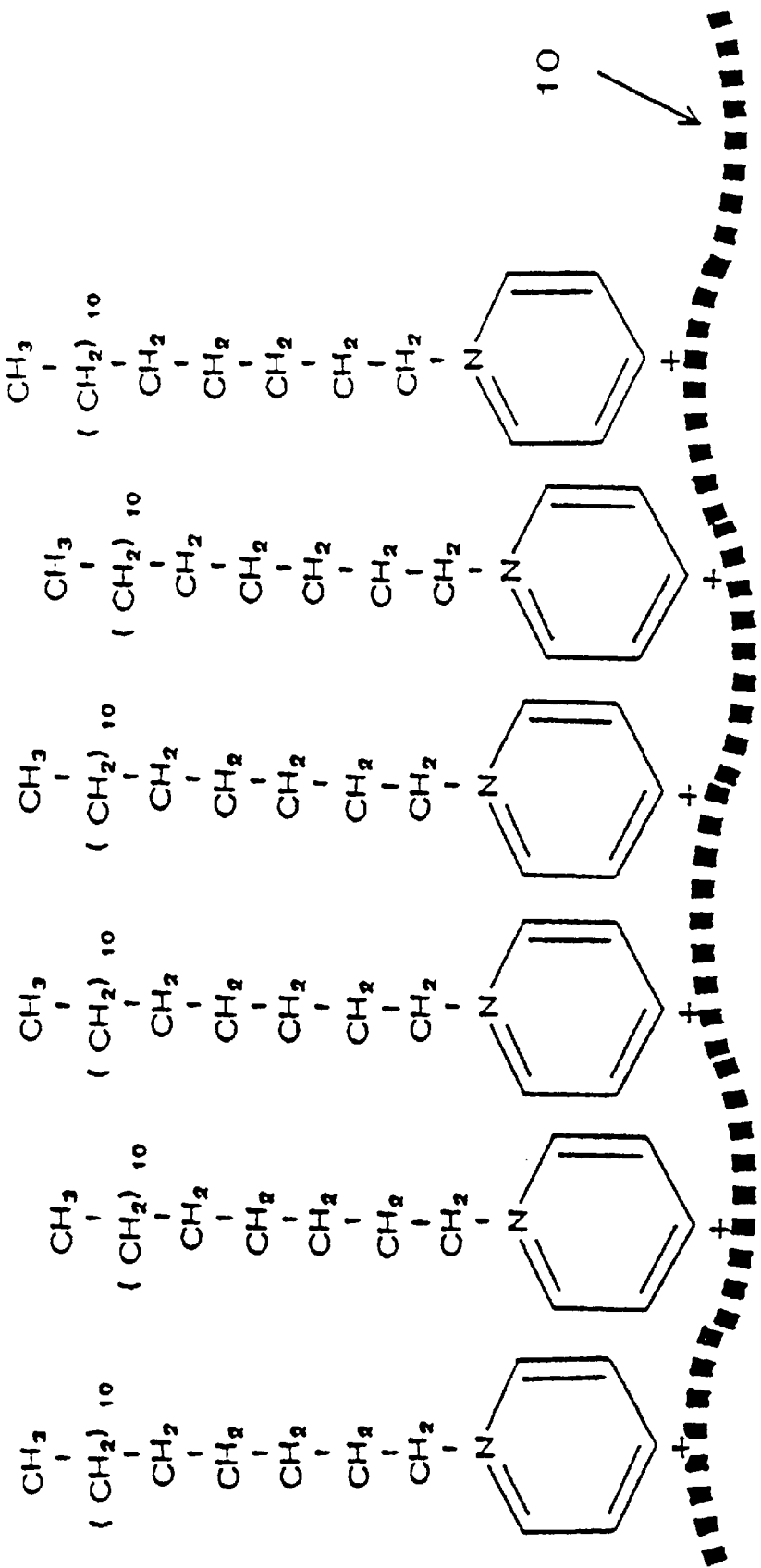

FIG. 4a depicts individual molecules of CPC, using the structural formulas. These molecules are individually bound to a mucin coat 10. The hydrophilic head groups of CPC are oriented toward and positioned proximal to the mucin coat 10. The hydrophobic hydrocarbon tails of CPC are oriented toward the bulk aqueous phase and are positioned distal to the mucin coat. The molecules of CPC are arranged in a collective manner in a linear array.

Figure 4B:
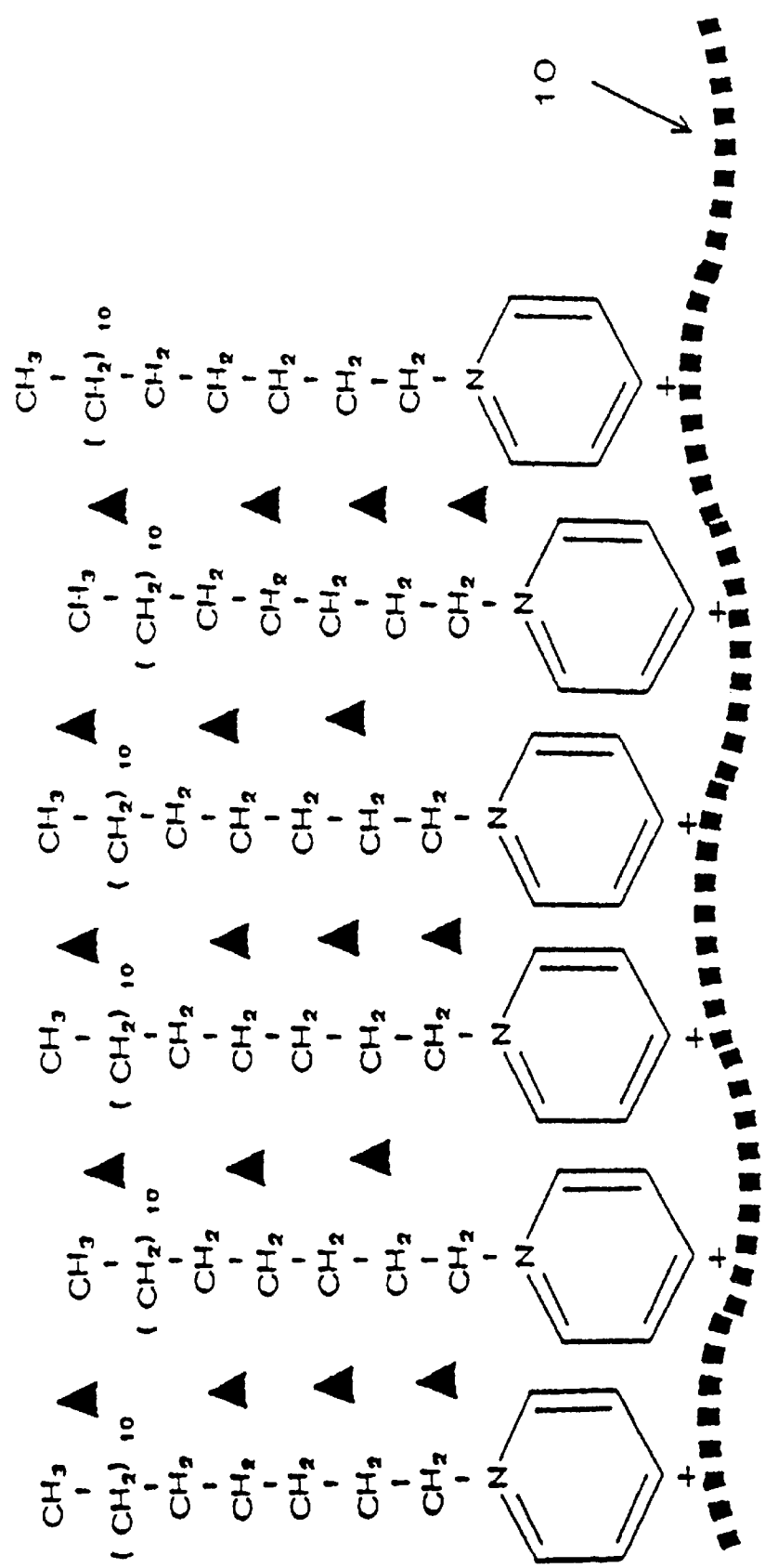

FIG. 4b illustrates the same phenomena as FIG. 4a with the further representation of p-aminobenzoic acid ethyl ester, represented by the symbol (▲), interspersed and trapped between the ordered hydrophobic chains of CPC.

Figure 5:
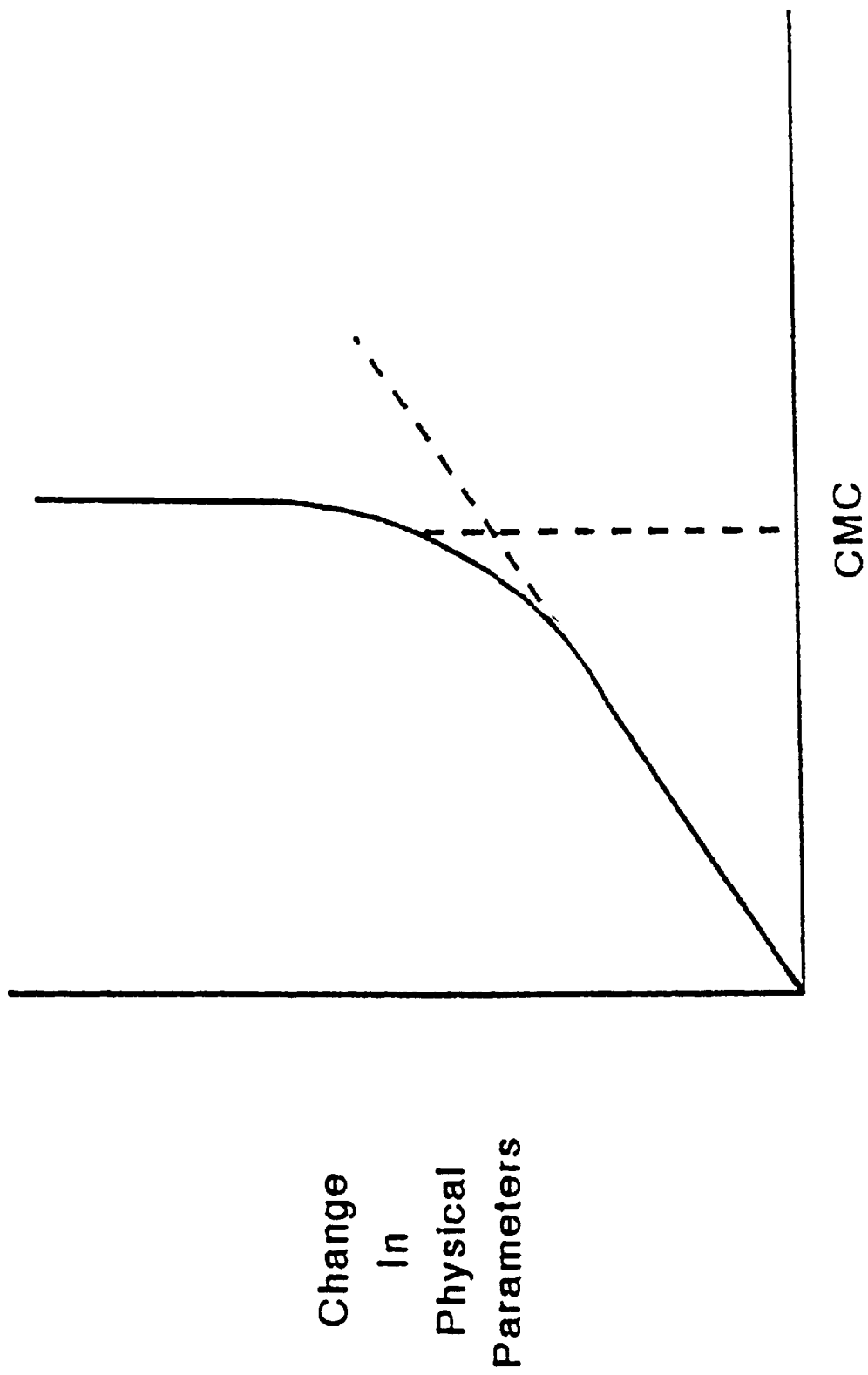

FIG. 5 is a graph which depicts the plot of the variation in physical properties of an amphiphile as a function of increasing amphiphile concentration. The critical micelle concentration is the point at which the structure of the amphiphile changes from the unassociated or free state to the micellar form.

Figure 6:
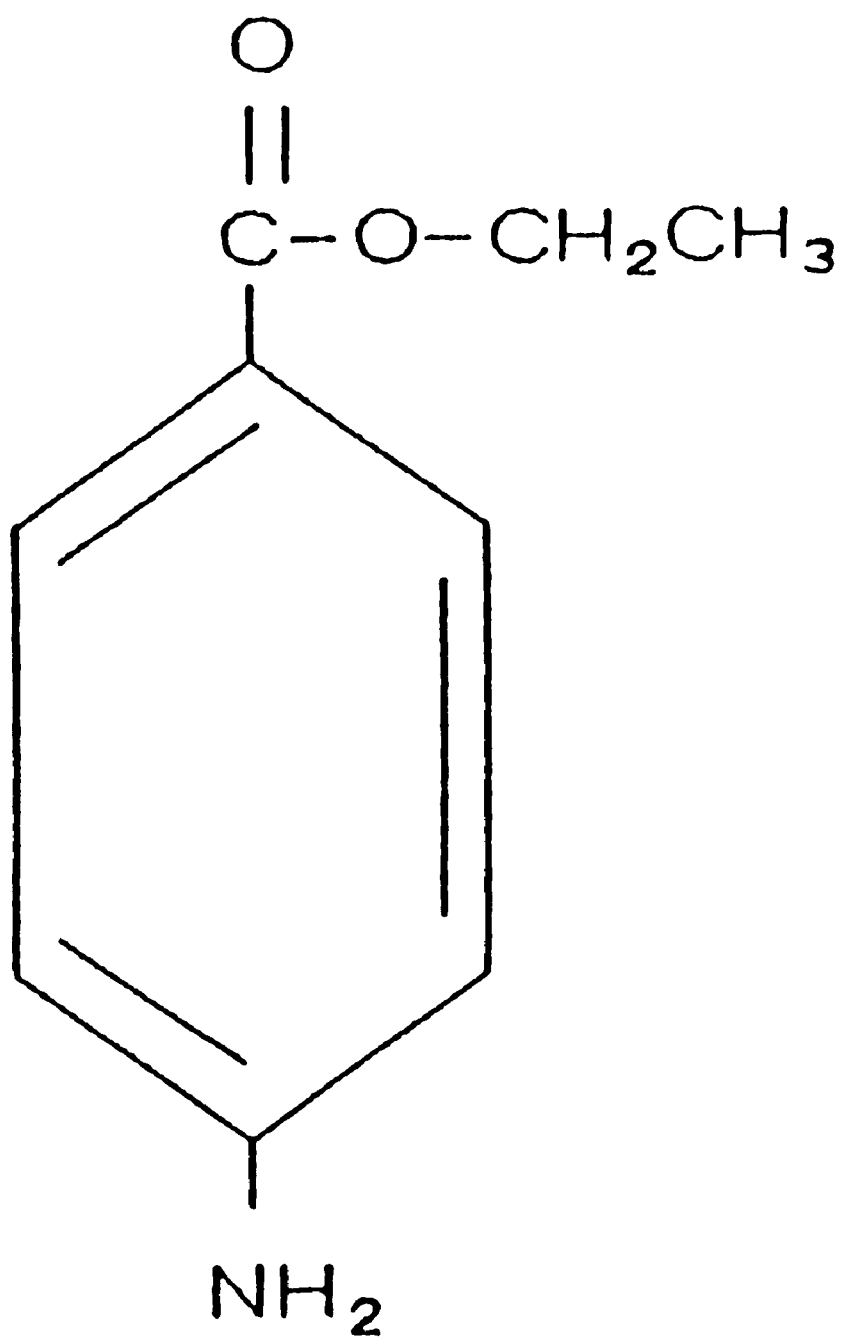

FIG. 6 is a representation of the structural formula for the topical anesthetic p-aminobenzoic acid ethyl ester.

Figure 7:
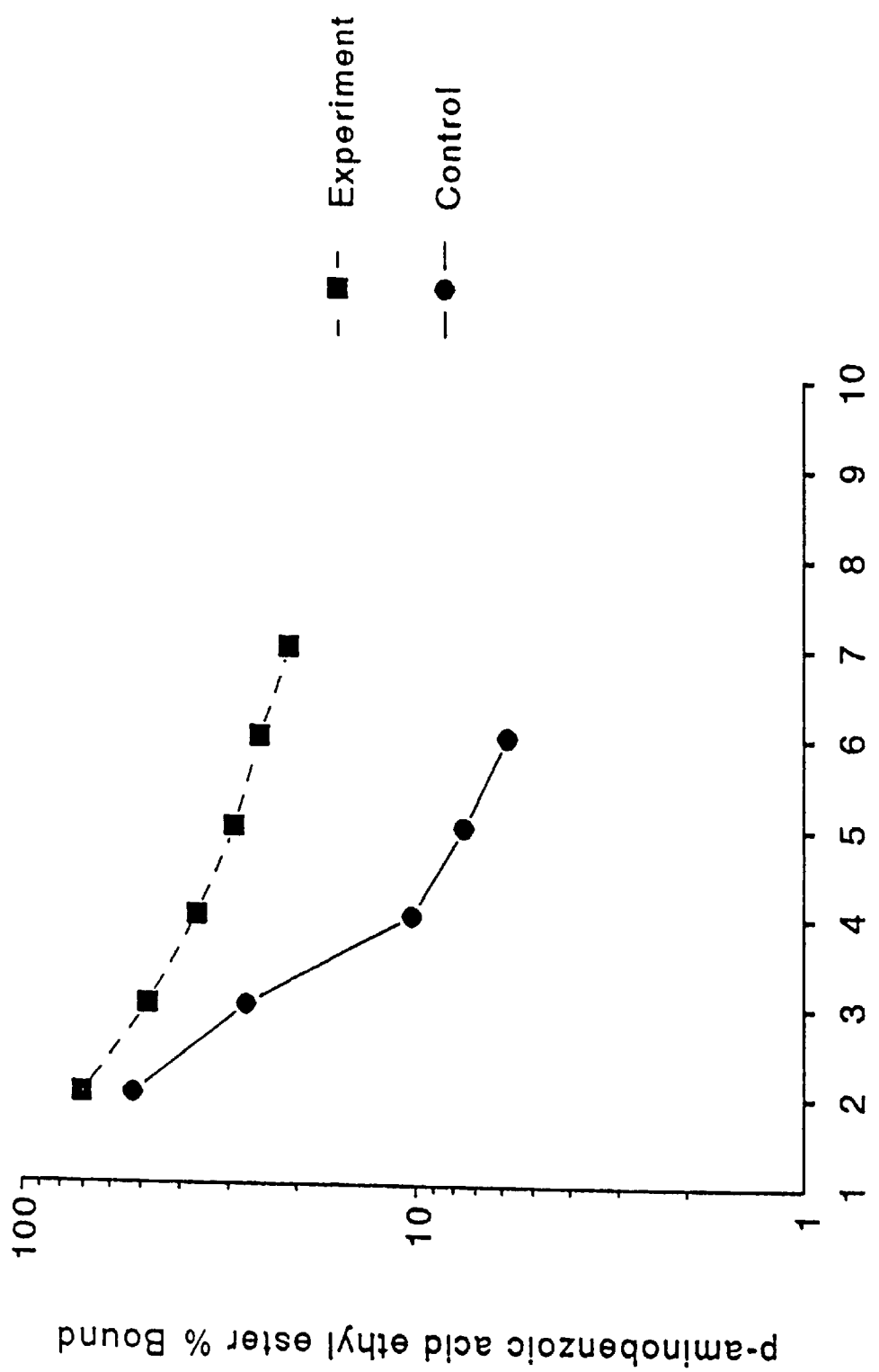

FIG. 7 is a graph wherein the percent of p-aminobenzoic acid ethyl ester, adhering to a mucin agarose gel, is plotted as a function of the number of 1.0 ml, 10 mM phosphate buffer pH 7.0 washes performed at ambient temperature. The legend (●) represents the control data where only p-aminobenzoic acid ethyl ester is added to the gel. The legend (■) represents the experimental data where p-aminobenzoic acid ethyl ester in the presence of CPC is added to the gel.

PREFERRED EMBODIMENT

This invention disclosure describes the discovery that molecules of cetyl pyridinium chloride (CPC) can function collectively to sequester organic molecules and comestibles, such as flavorants, pharmaceuticals or therapeutics. According to this invention, these organic molecules can be sequestered and then be slowly released, thereby, prolonging their duration of action. It has been demonstrated experimentally that flavorants such as menthol, and therapeutics such as the topical anesthetic p-aminobenzoic acid ethyl ester, can be sequestered within the hydrophobic regions of a CPC matrix. When the combination of CPC and the intended organic is administered to a warm-blooded host, strong adherence of the CPC to mucin, and a prolongation of action of the organic, is achieved. Examples of therapeutics that may be used in this intention are as follows: anesthetics, analgesics, antibiotics, antifungals, antitoxins, antihistamines, antineoplastics, antihelminthics, bronchial dilators, and ophthalmics.

Figure 1:
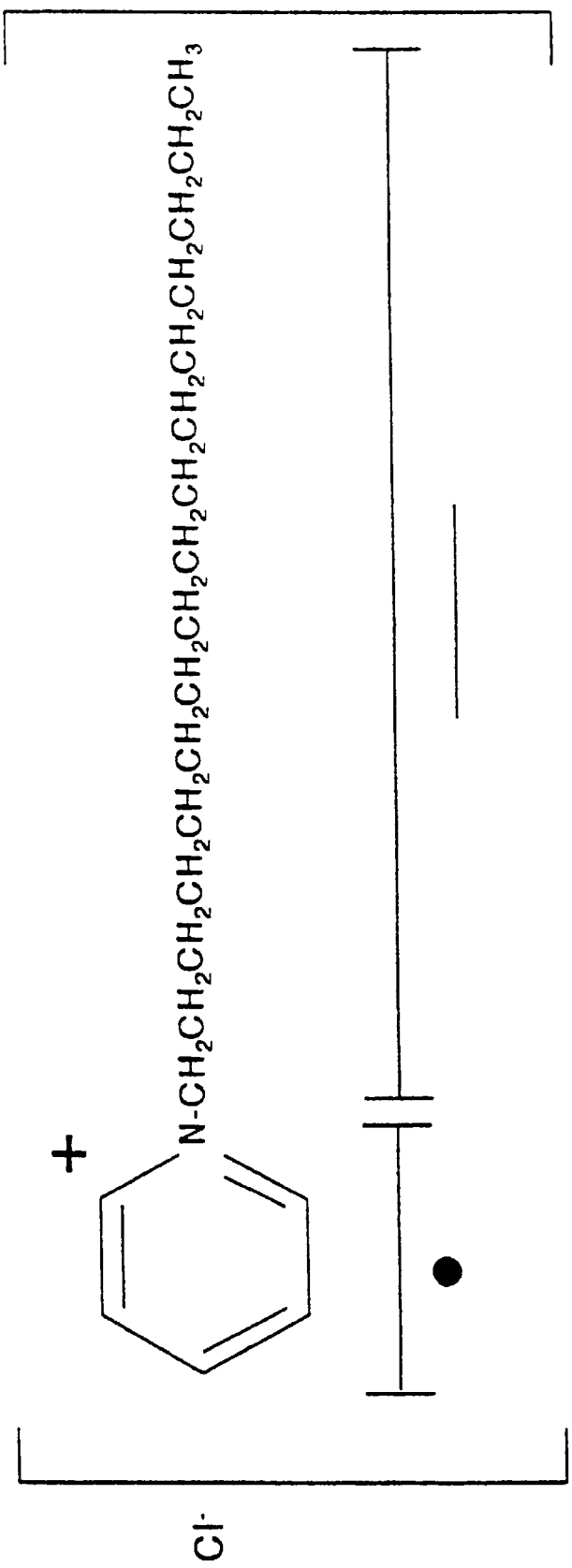
FIG. 1 is a representation of the structural formula of the amphiphilic molecule, cetyl pyridinium chloride.

Cetyl pyridinium chloride (CPC) is a quaternary ammonium compound and is a member of a class of cationic surfactants which contain a positively charged quaternary amine and an attached hydrophobic structure. The structure of CPC, which is illustrated in FIG. 1, shows a positively charged nitrogen atom contained within a pyridine ring which in turn is attached to a saturated straight chain alkyl group containing sixteen carbon atoms. Chemically, CPC is classified as an amphiphile. Cetyl pyridinium chloride has a critical micelle concentration (CMC) of 0.9 mM. Thus, at this concentration and above, the molecule is capable of forming molecular aggregations with other CPC molecules. However, this functional characteristic is expressed only under certain conditions. In dilute aqueous solutions of less than $10^{-4}$ or $10^{-5}$ M, the behavior of the CPC amphiphile parallels that of a strong electrolyte and exhibits properties applicable to this invention.

Conversely, at higher concentrations, the amphiphile exhibits a marked deviation in molecular and physical behavior. These deviations are observed as changes in structure and manifested as new physical-chemical properties. When CPC is prepared at concentrations above 0.9 mM, it is capable of self-association which results in the formation of structured micelles which can function as biological detergents.

Figure 2A:
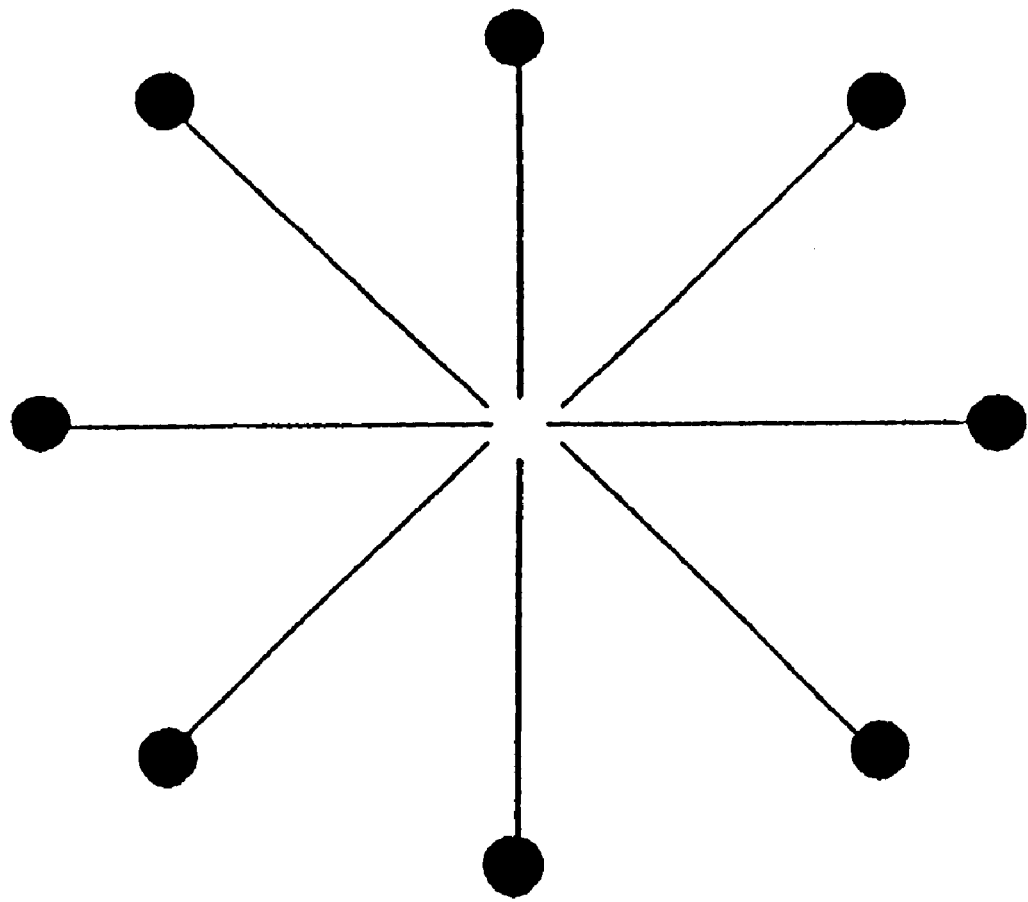
FIG. 2a is a diagrammatic representation of a spherical micelle cross-section where the symbol (●) represent the hydrophilic head group and the symbol (—) represents the hydrophobic tail group.
Figure 2B:
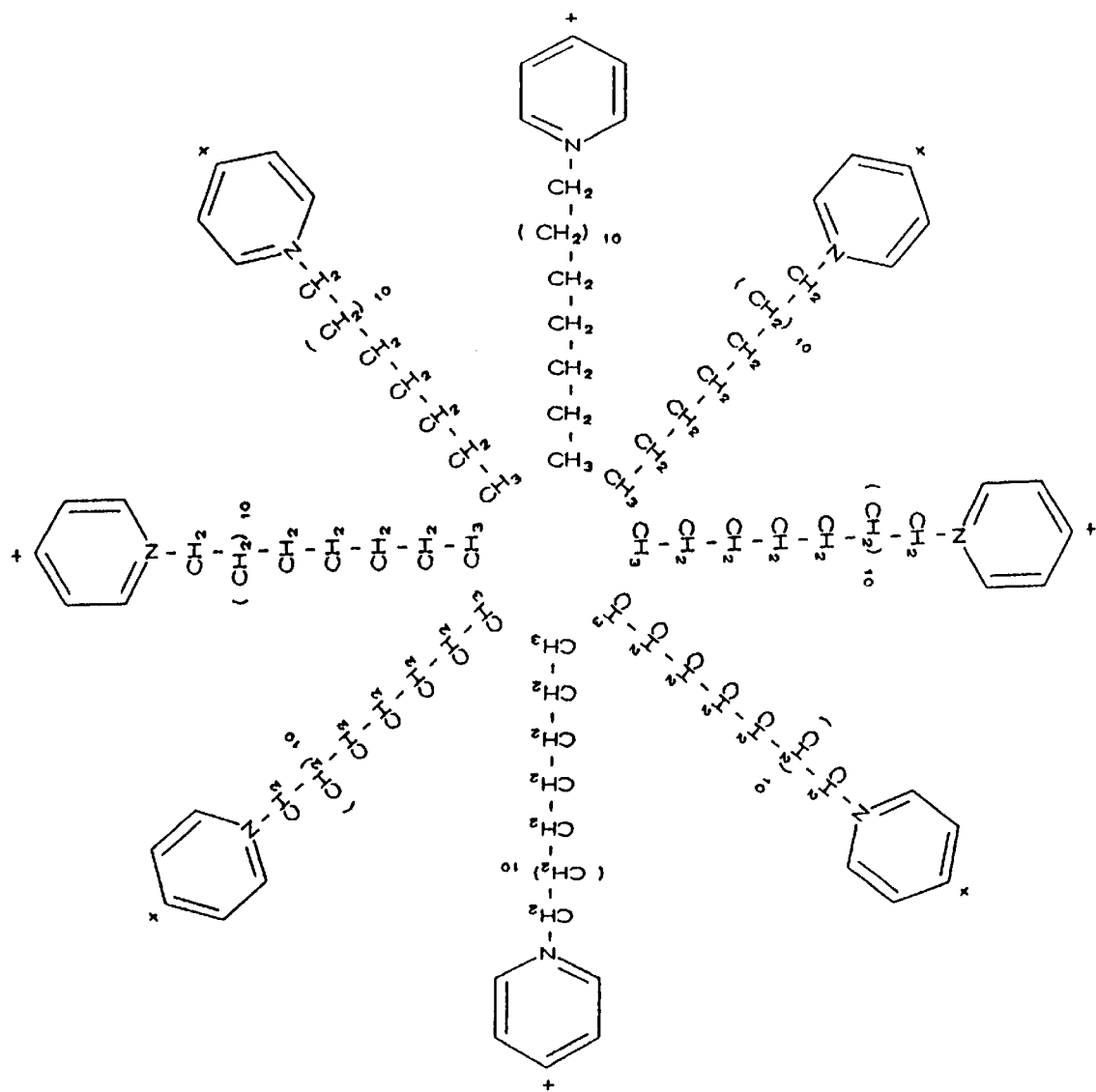
FIG. 2b is also representative of a spherical micelle cross-section. The individual amphiphilic molecular constituents are depicted using the structural formula of CPC.
Figure 3:
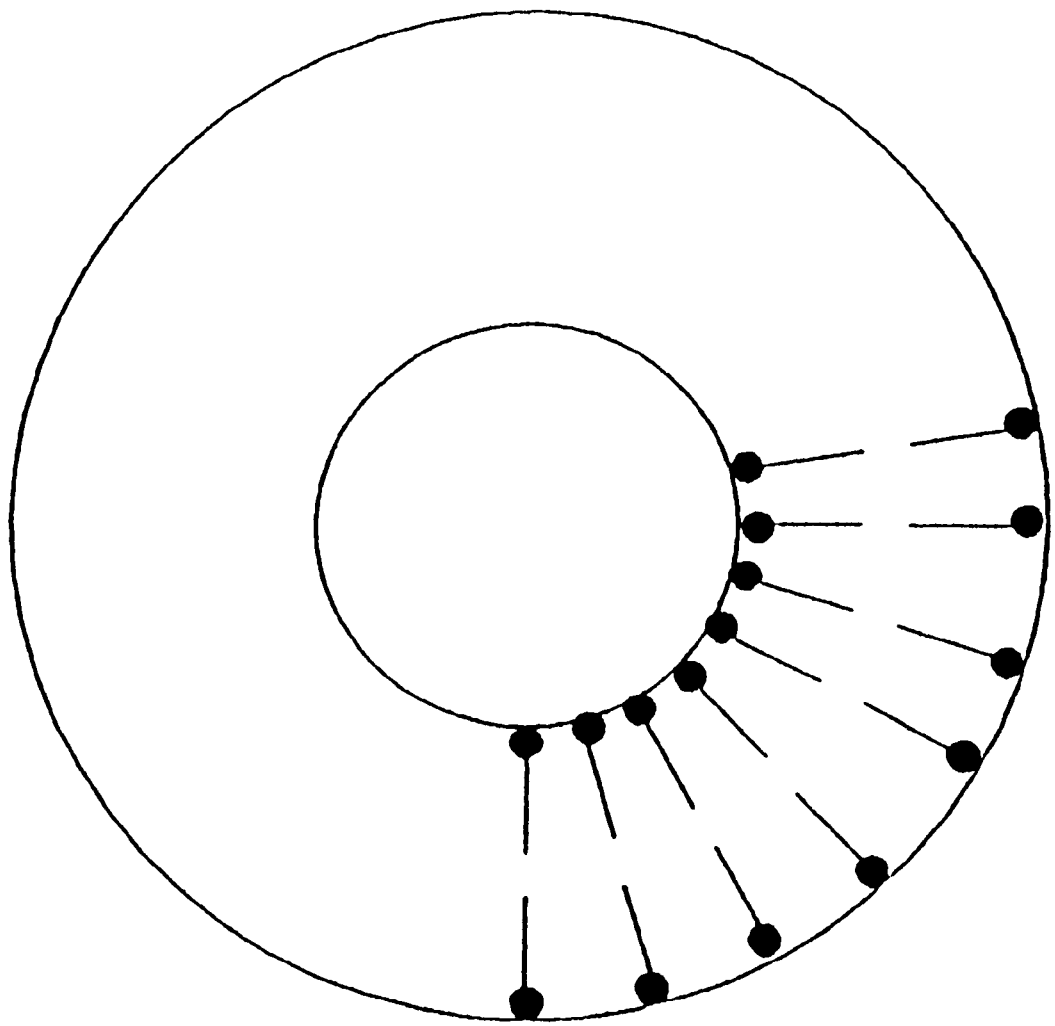
FIG. 3 illustrates a cross-section of a liposome depicting the bipolar lipid membrane structure with individual amphiphilic molecular constituents.

An example of the CPC micellar structure is shown in FIGS. 2a and b. FIG. 2a is a diagrammatic representation of a spherical micelle cross-section. FIG. 2b depicts the structural formula of CPC and is representative of a cross-sectional plane of the CPC micelle. The hydrophobic chains in the micelle are buried within the core of the micellar structure and are sequestered and inaccessible to the bulk aqueous phase environment. This structure is clearly differentiated from the structure of a bipolar lipid membrane, such as a liposomal membrane, which is shown only for comparison purposes in FIG. 3.

A liposomal membrane has the hydrophobic regions buried within the bipolar membrane structure. These regions are also inaccessible to the bulk aqueous phase environment.

This invention utilizes concentrations of amphiphile below the critical micelle concentration to enable the hydrophobic tail regions to function collectively and in concert with other CPC molecules, and be oriented toward the bulk aqueous phase. This collective structure is shown in FIG. 4a and provides a hydrophobic surface, positioned distally to the mucin coat. The exposed hydrophobic surface provides a sink in which organic molecules may be sequestered.

FIG. 5 is a graph which depicts the plot of the variations in physical properties of an amphiphile as a function of the increasing amphiphile concentration. A pronounced change in physical characteristics signaling the formation of micelles is indicated by the abrupt deviation from the linearity of the response curve as the critical micelle concentration (CMC) is approached. A change from the amphiphilic state to the micellar state is observed to occur at or near the CMC.

As a result of the increasing concentration, amphiphilic molecules begin to associate. Eventually micelles are formed. Some of the new physical and molecular properties manifested by the micelle are related to the interfacial tension, electrical conductivity, electromotive force, pH, density, specific heat, temperature coefficients of solubility, viscosity, and optical and spectroscopic properties of the solution.

These differences in structure and behavioral properties demonstrate that there is a marked contrast between an amphiphile exhibiting properties of an electrolyte (that is existing as freely rotating molecules in solution), and the same amphiphile at higher concentrations above the CMC functioning as a micelle.

The sink function is most likely achieved by some of the CPC molecules forming a cooperative interaction and sequestering organic substances among the alkyl chains. After the sink traps the flavorant such as menthol, the fluid of the host body then washes away the untrapped organic substance. This phenomena occurs at the same time the mint carrier, dissolves and is washed away. The trapped molecules also become exposed and gradually wash away, but at a slower rate than the untrapped molecules. Both the untrapped molecules and those trapped are exposed as the mint body dissolves, or a mouthwash flushes the oral cavity, but the cooperative interaction of the alkyl chains shields the trapped molecules to a degree sufficient to wash the last trapped molecules later than the untrapped, thus producing a prolonged effect.

This invention utilizes amphiphilic molecules in the free state, in the absence of micelles, to facilitate attachment to mucin coated surfaces and provides a continuous hydrophobic coating away from the mucin surface.

This invention focuses on utilizing the positive charge potential of the quaternary nitrogen atom of CPC to accentuate the binding of the amphiphile to mucin coated surfaces. It also utilizes an alkyl chain functionality for the sequestering of organics. The alkyl chain is covalently attached to the pyridinium ring in cetyl pyridinium chloride and functions as a sink, in concert with other chains for entrapping flavorant molecules, especially ones with volatile properties, such as menthol. Also, therapeutic agents, such as tricaine and p-aminobenzoic acid ethyl ester may be sequestered in the same manner.

In order for cetyl pyridinium chloride to function as a trapping agent for the organic molecules, the long alkyl chain must first be made accessible to the intended organic molecules. These chains then must be oriented in a collective linear array such that they can function in concert with neighboring CPC molecules. This concept is shown in FIG. 4a. In this manner, flavorant can become entrapped or intercalated between the alkyl chains and sequestered for an undetermined period of time.

The chemistry of the interaction requires that the concentration of cetyl pyridinium chloride be maintained below the critical micelle concentration of 0.9 mM, or 247 ppm. Under these conditions, the structure illustrated in FIG. 4a will predominate and exist independently of any micelle formation.

High concentrations of CPC results in micellar formation that permits strong surfactant like properties to emerge and dominate in solution. Micellar structure, as dictated by the laws of surface chemistry, will present a positively charge pyridinium ion shield as illustrated in FIG. 2b. The structure of FIG. 2b would not facilitate the sequestering of organic flavorants or therapeutics such as p-aminobenzoic acid ethyl ester or tricaine on mucin surfaces.

Thus, a provision of this invention is that the concentration of CPC be kept below the critical micelle concentration when in actual use on a mucin surface. This enables the molecules of cetyl pyridinium chloride with the positively charged quaternary ammonium ions and attached alkyl chains to line up in a linear array at the mucin surface. The alkyl chains provide a contiguous and continuous matrix of hydrophobicity to be exposed outwardly and be positioned distally to the mucin surface. These exposed hydrophobic groups provide for the sequestration of selected organic molecules according to this invention.

Once the CMC of cetyl pyridinium chloride is exceeded by a factor of two or more, a very noticeable and marked astringency sensation is observed. There is a constricting or compressing of the mucus coated tissues in the oral cavity which results in this bitter astringency. Consequently, there are constraints on how high the concentration of cetyl pyridinium chloride may be increased before it lacks utility.

The solid breath mint and the therapeutic p-aminobenzoic acid ethyl ester formulations utilize CPC at concentrations around the CMC. The concentrations of CPC in the mint is in a range of 0.4 to 0.6 mg CPC per 1800 mg total of mint or 0.0222% to 0.0333% by weight respectively. If this amount of CPC were to be immediately solubilized in 1.0 ml aqueous media such as saliva, the critical micelle concentration would be quickly achieved and undesirable binding problems would be observed as well as undesirable taste perceptions. However, by incorporation sweeteners such as aspartame, and bulking agents such as sorbitol, the solubilization of CPC is retarded because the mint dissolves slowly. Hence, the critical micelle concentration of CPC is never achieved during actual taste testing.

The solid mint form, and the liquid form, are nevertheless the same inventive concept. When used in the liquid form, the mixing of p-aminobenzoic acid, and cetyl pyridinium chloride will entrap some of the organic substance within the pyridinium tail group. Then, as the liquid is dispensed, it will carry the non-trapped active ingredient and some of the CPC, with the entrapped active ingredient, thus extending the effectiveness of the application of p-aminobenzoic acid.

BEST MODE

In the manufacture of mints, the CPC is initially solubilized in flavorant. This is an example of solubilizing one organic constituent in another. When these constituents are added to the mint components, the molecules of cetyl pyridinium chloride freely rotate with the flavorant organics and are continually mixed around one another. When the mint is slowly solubilized in the oral cavity over a 5 to 10 minute period, the positively charged pyridinium ions and the long hydrophobic tails of CPC in accompaniment with the flavorant molecules bind to the mucin coated surfaces of the oral cavity.

Experimentally, it has been observed that the formulation of cetyl pyridinium chloride into peppermint oil with sorbitol as a bulking agent, plus an added sweetener, such as aspartame, forms a unique mint construct. These additive ingredients work together in a collective manner to provide prolongation of flavor. These effects have been observed and recorded in a blind study by a taste test panel. The results from this study showed that the mint formulation provided a superior, longer tasting, and fresher mint product. The undesirable characteristics of after taste and astringency that may accompany other products are absent from this formulation. The results from the study that utilized the topical anesthetics p-aminobenzoic acid ethyl ester were equally convincing.

The structural formula of p-aminobenzoic acid ethyl ester synonym: ethyl amino benzoate is shown in FIG. 6. Because of its chemical properties, p-aminobenzoic acid ethyl ester can be intercalated between the alkyl chains of cetyl pyridinium chloride. FIG. 4b illustrates how cetyl pyridinium chloride when bound to a mucin surface in an linear array permits p-aminobenzoic acid ethyl ester to be interspersed and entrapped between the hydrophobic chains.

When a mucin gel is prepared by binding mucin covalently to a cyanogen bromide activated sephrose, a mucin matrix is created that allows binding of cetyl pyridinium chloride.

The graph in FIG. 7 illustrates a controlled experiment in which 50 µg of p-aminobenzoic acid ethyl ester was added to a mucin gel and then easily washed away. This same figure shows results using an experimental sample as indicated by the legend: (■) which was prepared using the same amount (50 µg) of p-aminobenzoic acid ethyl ester, along with cetyl pyridinium chloride. The concentration of CPC was below the CMC.

This graph of FIG. 7 illustrates that the control, with only p-aminobenzoic acid ethyl ester, washes away from mucin gel in a much more rapid fashion than the combination of p-aminobenzoic acid ethyl ester and CPC. The results indicate that cetyl pyridinium chloride has a special adherence property which facilitates binding of the molecule to mucin. Furthermore, a concomitant benefit is realized by retarding the washing away of p-aminobenzoic acid ethyl ester. The differences observed in the binding experiment between the control and experimental preparations illustrate an exceptional example of the usefulness of this invention.

The structural formula of p-aminobenzoic acid ethyl ester in FIG. 6 depicts a primary amino group in the para position of the aminobenzoic acid ethyl ester benzene ring. This amino group becomes positively charged as the pH decreases. However, as supported by the data in FIG. 7, even this positive charge is not strong enough to hold the p-aminobenzoic acid ethyl ester on the inucin surface for a prolonged period of time. However, cetyl pyridinium chloride has a positive charge that is active and continually present in the pyridinium ring. This positive charge is independent of the pH. This graph illustrates clearly that cetyl pyridinium chloride is functioning as a mucin adhering agent. The fact that p-aminobenzoic acid ethyl ester can be held, or bound, or intercalated in CPC is a clear indication that this topical anesthetic can be made to adhere to mucin surfaces utilizing the correct formulation of CPC and active. The binding of p-aminobenzoic acid ethyl ester may thereby be prolonged and the duration of its pharmacological action extended. These effects should have a pronounced benefit for the consumer or the patient who uses p-aminobenzoic acid ethyl ester products with the correct and optimum levels of cetyl pyridinium chloride.

Having established the reliable time extension, using menthol and p-amino benzoic acid, it is only a matter of selecting one of the listed substitutes. The CPC was chosen for this disclosure, because it alone in the class, is established to be toxin free for human use.

A benefit conferred is the time-release leaching of the topical anesthetic agent from the CPC matrix. A further elaboration of the concept disclosed for cetyl pyridinium chloride also maintains for the following quaternary ammonium compounds: cetyl konium chloride, cetyl dimethyl ethyl ammonium bromide, benzyl triethyl ammonium chloride, cetyl trimethyl ammonium para toluene sulfonate, cetyl trimethyl ammonium bromide, distearyl dimethyl ammonium methosulfate, tetra n-butylammonium bromide, myristyl trimethyl ammonium bromide, cetyl dimethyl benzyl ammonium chloride, cetyl pyridinium bromide, cetyl trimethyl ammonium chloride, stearyl dirriethyl benzyl ammonium chloride, cetyl trimethyl ammonium stearate, benzal konium chloride, domiphen bromide, and methyl benzethonium chloride.

The chemistry of this invention is not simple, the basic concept is easy to understand once conceived. The object is to hold an organic substances such as menthol, for slow release to extend the effective time of action of a flavorant or therapeutic for example.

The principle concern of this concept is the oral cavity of a warm-blooded host, but can be applied to any mucin surface.

The discovery was that CPC molecules can be caused to associate on a mucin surface in a lateral array as shown in FIG. 4a, by manipulating the concentration of CPC within close limits. At low concentrations, a molecule of CPC is a freely floating entity, forming a regular structure.

A concentration above determined limits will cause the CPC molecule to form micelles, which presents a closed system incapable of holding the desired organic flavorant or other desired substance.

Once the CPC and flavorant are administered to the oral cavity, the saliva will disperse the flavorant. Initially, the saliva will disperse the free flavorant molecules. Then after a time, it will disperse the flavorant emeshed within the CPC tails.

What is claimed is:

1. A process for extending the effective time of action of an organic substance available from a designated dose, comprising:

entrapping the organic substance dose in a sink of hydrophobic chains of cetyl pyridinium chloride molecules, wherein the cetyl pyridinium chloride molecules are present in a concentration less than that required for micelle formation and bind to mucin;

whereby, a portion of the organic substance is freed from entrapment by the hydrophobic chains of cetyl pyridinium chloride molecules over time as the balance of non-entrapped organic substance is dissipated by a fluid wash.

2. A process for extending the effective time of action of an organic substance available from a designated dose, comprising the steps of:

combining the organic substance with one or more cetyl pyridinium chloride molecules, wherein the active organic substance is trapped by hydrophobic chains attached to pyridinium moieties expressed by the cetyl pyridinium chloride molecules;

said cetyl pyridinium chloride molecules being present in a proportion less than that required for micelle formation and having an affinity to bind to mucin;

whereby, the organic active substance not trapped by the cetyl pyridinium chloride molecules is depleted and that trapped by the cetyl pyridinium chloride hydrocarbon chains is sequestered, thereby prolonging the action of the organic substance.

3. A process for prolonging the activity of a designated dose of an organic substance on a mucin surface of a warm-blooded animal comprising the steps of:

a) providing cetyl pyridinium chloride having a water-soluble hydrophilic head and a water-insoluble hydrophobic organic tail, wherein said cetyl pyridinium chloride is present in an amount less than its critical micelle concentration;

b) mixing said cetyl pyridinium chloride with a designated dose of an organic substance thereby sequestering the organic substance within the hydrophobic tail of the cetyl pyridinium chloride; and, c) administering the cetyl pyridinium chloride-organic substance mixture to a mucin surface of a warm-blooded host, wherein the hydrophilic head of the cetyl pyridinium chloride is adhered to the mucin surface and the hydrophobic tail of the cetyl pyridinium chloride sequesters the organic substance thereby prolonging the activity of the organic substance.

4. The method of claim 3, wherein the organic substance is selected from the group consisting of flavorant and therapeutic organic molecules.

5. The method of claim 4, wherein the therapeutic organic molecule is selected from the group consisting of anesthetic, analgesic, antibiotic, antifungal, antitoxin, antihistamine, antineoplastic, antihelminthic, bronchial dilator and optithalmic organic molecules.

6. The method of claim 4, wherein the therapeutic organic molecule is selected from the group consisting of tricaine and p-aminobenzoic acid ethyl ester.

7. The method of claim 3, wherein the critical micelle concentration of the cetyl pyridinium chloride is 0.9 mM.

8. The method of claim 4, wherein the organic flavorant is peppermint oil.

9. The method of claim 3, wherein the amphophilic substance is selected from the group consisting of cetyl konium chloride, cetyl dimethyl ethyl ammonium bromide, benzyl triethyl ammonium chloride, cetyl trimethyl ammonium para toluene sulfonate, cetyl trimethyl ammonium bromide, distearyl dimethyl ammonium methosulfate, tetra n-butylammonium bromide, myristyl trimethyl ammonium bromide, cetyl dimethyl benzyl ammonium chloride, cetyl pyridinium bromide, cetyl trimethyl ammonium chloride, stearyl dimethyl benzyl ammonium chloride, cetyl trimethyl ammonium stearate, benzal konium chloride, domiphen bromide, and methyl benzethonium chloride.

10. A process for prolonging the activity of a designated dose of an organic therapeutic compound on a mucin coated surface of a warm-blooded animal comprising the steps of:

a) providing an amphophilic substance having a water-soluble hydrophilic polar head and a water-insoluble hydrophobic organic tail, wherein said amphophilic substance is present in an amount below its critical micelle concentration, and wherein said amphophilic substance has the ability to adhere to a mucin surface at its hydrophilic head and to sequester an organic therapeutic compound at its hydrophobic tail;

b) mixing with the amphophilic substance a designated dose of an organic therapeutic compound wherein the organic therapeutic compound becomes sequestered to the hydrophobic tail of the amphophilic substance; and, c) applying the mixture to a mucin surface and allowing for a sufficient period of time for the amphophilic substance to be adhered by its hydrophilic head to a mucin coated surface thereby inhibiting fluid wash and prolonging the activity of the sequestered organic therapeutic compound.

11. The method of claim 10, wherein said amphiphic substance is cetyl pyridinium chloride.

12. The method of claim 10, wherein said mucin surface is selected from a group of mucin coated surfaces present in the oral cavity, esophagus, eye, vagina, bladder, rectal cavity and stomach of the warm blooded animal.

13. The method of claim 10, wherein said organic therapeutic compound is P-aminobenzoic acid ethyl ester.

14. The method of claim 10, wherein said critical micelle concentration is the point at which the structure of the amphiphile substance changes from the unassociated state to the micellar form.

15. The method of claim 10, where said amphophilic substance is selected from the group consisting of cetyl konium chloride, cetyl dimethyl ethyl ammonium bromide, benzyl triethyl ammonium chloride, cetyl trimethyl ammonium para toluene sulfonate, cetyl trimethyl ammonium bromide, distearyl dimethyl ammonium methosulfate, tetra n-butylammonium bromide, myristyl trimethyl ammonium bromide, cetyl dimethyl benzyl ammonium chloride, cetyl pyridinium bromide, cetyl trimethyl ammonium chloride, stearyl dimethyl benzyl ammonium chloride, cetyl trimethyl ammonium stearate, benzal konium chloride, domiphen bromide, and methyl benzethonium chloride.

* * * * *